United States Patent
Majumder et al.

(10) Patent No.: US 8,609,916 B2
(45) Date of Patent: Dec. 17, 2013

(54) PROCESSES FOR PREPARING ALKYLATED AROMATIC COMPOUNDS

(75) Inventors: Debarshi Majumder, Chicago, IL (US); Carl John Stevens, Lake Forest, IL (US); Robert James Schmidt, Barrington, IL (US)

(73) Assignee: UOP LLC, Des Plaines, IL (US)

( * ) Notice: Subject to any disclaimer, the term of this patent is extended or adjusted under 35 U.S.C. 154(b) by 116 days.

(21) Appl. No.: 13/418,133

(22) Filed: Mar. 12, 2012

(65) Prior Publication Data

US 2013/0237731 A1     Sep. 12, 2013

(51) Int. Cl.
*C07C 2/66* (2006.01)

(52) U.S. Cl.
USPC .......................................... 585/449; 585/467

(58) Field of Classification Search
USPC .................................. 585/449, 467
See application file for complete search history.

(56) References Cited

U.S. PATENT DOCUMENTS

| | | |
|---|---|---|
| 4,870,222 A * | 9/1989 | Bakas et al. .................. 585/323 |
| 4,885,412 A | 12/1989 | Pennington et al. |
| 5,908,962 A | 6/1999 | Zakoshansky et al. |
| 6,008,422 A | 12/1999 | Schulz et al. |
| 6,384,153 B2 | 5/2002 | Hammer et al. |
| 7,498,471 B2 | 3/2009 | Schultz et al. |
| 2010/0300930 A1 | 12/2010 | Clark et al. |
| 2011/0245558 A1 | 10/2011 | Schmidt |

OTHER PUBLICATIONS

Barthe, P., et al., "Continuous multi-injection reactor for multipurpose production—Part I," Chemical Engineering and Technology, vol. 31, No. 8, pp, 1146-1154; Aug. 2008.

* cited by examiner

*Primary Examiner* — Thuan D Dang
(74) *Attorney, Agent, or Firm* — Mark R Willis (57) ABSTRACT

Processes for preparing alkylation aromatic compounds are provided. One process for preparing alkylated aromatic compounds includes reacting an aromatic compound and an olefin in at least one primary alkylation reaction in the presence of a first alkylation catalyst to produce a first effluent. The first effluent is split into a first product-rich stream and a first recycle stream, and the first recycle stream is recycled to the at least one primary alkylation reaction. Unreacted aromatic compound from the first product-rich stream and an additional olefin are reacted in at least one downstream alkylation reaction in the presence of a second alkylation catalyst to produce a second effluent. The second effluent is split into a second product-rich stream and a second recycle stream, and the second recycle stream is recycled to the at least one primary alkylation reaction and, optionally, to the at least one downstream alkylation reaction.

11 Claims, 5 Drawing Sheets

PROCESSES FOR PREPARING ALKYLATED AROMATIC COMPOUNDS

TECHNICAL FIELD

The present invention generally relates to processes for preparing alkylated aromatic compounds and, more particularly, relates to processes for maximizing selectivity of monoalkyl aromatic compounds during preparation of alkylated aromatic compounds.

BACKGROUND

The alkylation of aromatic compounds with olefins to produce monoalkyl aromatic compounds is a well-developed process that is practiced commercially in large industrial units. One commercial application of this process is the alkylation of benzene with ethylene to produce ethylbenzene, which may subsequently be used to produce styrene. Another application is the alkylation of benzene with propylene to form cumene (isopropylbenzene), which may subsequently be used in the production of phenol and acetone. Those skilled in the art are therefore familiar with the general design and operation of such alkylation processes.

Alkylation processes generally involve alkylation of aromatic compounds with olefins in the presence of alkylation catalyst. In particular, it is known to conduct alkylation processes in a multi-bed alkylation reactor that includes at least two separate alkylation stages, with the alkylation stages each including an alkylation catalyst bed. Such multi-bed alkylation reactors can be effectively utilized to maximize yield of alkylation products. To maximize a useful life of conventional alkylation catalysts, techniques have been developed for maintaining reaction temperatures in the separate alkylation stages within a particular temperature range, with little difference in reaction temperature between the various alkylation stages. Under uncontrolled conditions, reaction temperatures tend to be highest in the first alkylation stage due higher reaction rates prevalent therein. Because less available unreacted aromatic compounds are generally present in downstream alkylation stages, reaction rates and, thus, reaction temperatures tend to be lower in downstream alkylation stages.

To enable greater temperature control in the various alkylation stages, one development that has been made is to recycle unreacted aromatic compounds from product effluent to both the first alkylation stage and to downstream alkylation stages in the alkylation reactor. For example, it is known to distill unreacted aromatic compounds from the product effluent, followed by recycling the unreacted aromatic compounds to the various alkylation stages in the alkylation reactor. In this manner, reaction rates and reaction temperatures can be controlled in the various alkylation stages. It is also known to recycle some of the reactor effluent to the various alkylation stages, without distilling the unreacted aromatic compounds, also for purposes of controlling temperatures in the various alkylation stages of the multi-bed alkylation reactors.

Despite the developments involving recycling reactor effluent and/or unreacted aromatic compounds that have been proposed to date, selectivity of monoalkyl aromatic compound formation is impacted by such developments. In particular, recycling of the reactor effluent can result in a higher incidence of dialkyl- and/or trialkyl-aromatic compound formation. The reactor effluent generally includes large quantities of monoalkyl aromatic compounds, and returning such monoalkyl compounds to the various alkylation stages risks further reaction of the monoalkyl aromatic compounds to produce the dialkyl- and/or trialkyl-aromatic compounds, thereby decreasing selectivity of monoalkyl aromatic compound formation. Further, techniques that involve distilling the unreacted aromatic compounds from the product effluent, followed by recycling the unreacted aromatic compounds to the various alkylation stages in the alkylation reactor, as described above, require significant energy expenditures to vaporize and condense the unreacted aromatic compounds. While selectivity of monoalkyl aromatic compound formation can be increased by increasing a ratio of aromatic compound to olefin, lower ratios of aromatic compound to olefin are desirable from an energy cost standpoint.

Accordingly, it is desirable to provide processes for preparing alkylated aromatic compounds that enable maximized selectivity of monoalkyl aromatic compounds to be achieved while recycling reactor effluent that includes the desirable monoalkyl aromatic compounds present therein. It is also desirable to provide such processes that enable maximized selectivity of monoalkyl aromatic compounds to be achieved without increasing a ratio of aromatic compound to olefin. Furthermore, other desirable features and characteristics of the present invention will become apparent from the subsequent detailed description of the invention and the appended claims, taken in conjunction with the accompanying drawings and this background of the invention.

BRIEF SUMMARY

Processes for preparing alkylation aromatic compounds are provided herein. In an embodiment, a process for preparing alkylated aromatic compounds includes reacting an aromatic compound and an olefin in a at least one primary alkylation reaction in the presence of a first alkylation catalyst to produce a first effluent that includes an alkylated aromatic compound and an unreacted aromatic compound. The first effluent is split into a first product-rich stream and a first recycle stream, and the first recycle stream is recycled to the at least one primary alkylation reaction. The unreacted aromatic compound from the first product-rich stream and an additional olefin are reacted in at least one downstream alkylation reaction in the presence of a second alkylation catalyst to produce a second effluent including the alkylated aromatic compound. The second effluent is split into a second product-rich stream and a second recycle stream, and the second recycle stream is recycled to the at least one primary alkylation reaction and, optionally, to the at least one downstream alkylation reaction.

In another embodiment, a process for preparing alkylated aromatic compounds is conducted in an alkylation apparatus that includes at least one primary alkylation catalyst bed and at least one downstream alkylation catalyst bed. The process includes introducing an aromatic compound and an olefin into the at least one primary alkylation catalyst bed under alkylation conditions to produce a first effluent that includes an alkylated aromatic compound and an unreacted aromatic compound. The first effluent is split into a first product-rich stream and a first recycle stream, and the first recycle stream is recycled to the at least one primary alkylation reaction. The first product-rich stream and an additional olefin are introduced into the at least one downstream alkylation catalyst bed under alkylation conditions to produce a second effluent that includes the alkylated aromatic compound. The second effluent is split into a second product-rich stream and a second recycle stream, and the second recycle stream is recycled to the at least one primary alkylation catalyst bed and, optionally, to the at least one downstream alkylation catalyst bed.

In another embodiment, a process for preparing alkylated aromatic compounds includes reacting an aromatic compound and an olefin in a at least one primary alkylation reaction in the presence of a first alkylation catalyst to produce a first effluent that includes an alkylated aromatic compound and an unreacted aromatic compound. The first effluent is split into a first product-rich stream and a first recycle stream, and the first recycle stream is recycled only to the at least one primary alkylation reaction. The unreacted aromatic compound from the first product-rich stream and an additional olefin are reacted in at least one downstream alkylation reaction in the presence of a second alkylation catalyst to produce a second effluent including the alkylated aromatic compound. The second effluent is split into a second product-rich stream and a second recycle stream, and the second recycle stream is recycled to the at least one primary alkylation reaction and to the at least one downstream alkylation reaction. The first recycle stream substitutes a portion of the second recycle stream that is recycled to the at least one primary alkylation reaction.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. Furthermore, there is no intention to be bound by any theory presented in the preceding background or the following detailed description.

Processes for preparing alkylated aromatic compounds are provided herein in which an aromatic compound and an olefin are reacted in at least one primary alkylation reaction to produce a first effluent including an alkylated aromatic compound and an unreacted aromatic compound. The first effluent is split into a first recycle stream and a first product-rich stream, which have the same chemical make-up as the first effluent. Unreacted aromatic compound from the first product-rich stream and an additional olefin are reacted in at least one downstream alkylation reaction to produce a second effluent. The second effluent is split into a second product-rich stream and a second recycle stream, which have the same chemical make-up as the second effluent. The processes described herein enable maximized selectivity of monoalkyl aromatic compounds to be achieved by recycling the first recycle stream to the at least one primary alkylation reaction and recycling the second recycle stream to the at least one primary alkylation reaction and, optionally, to the at least one downstream alkylation reaction. For purposes of this disclosure, "selectivity" means the ratio of moles of monoalkyl aromatic compounds to moles of all alkylated aromatic compounds (e.g., monoalkyl-, dialkyl-, and trialkyl-aromatic compounds) produced through the process. Selectivity can also be measured as a ratio or percentage of moles of monoalkyl aromatic compounds to moles of olefin that are reacted with the aromatic compound. Because the first recycle stream is taken upstream of the second recycle stream, the first recycle stream has less alkylated aromatic compounds present therein than the second recycle stream. Also, because monoalkyl aromatic compounds that are introduced into the at least one primary alkylation reaction through the first recycle stream and the second recycle stream are exposed to alkylation conditions in not only the at least one primary alkylation reaction but also in the at least one downstream alkylation reaction, the monoalkyl aromatic compounds are prone to further alkylation to produce multiple alkylated by-products such as dialkyl- and/or trialkyl-aromatic compounds. The multiple alkylated by-products are generally recovered and recycled in a downstream transalkylation section in order to convert such compounds back to the desired primary monoalkyl aromatic compound. By recycling the first recycle stream to the at least one primary alkylation reaction along with recycling the second recycle stream to the at least one primary alkylation reaction, the reintroduction of at least some of the monoalkyl aromatic compounds from the second recycle stream into the full series of alkylation reactions can be minimized, thereby decreasing the production of dialkyl- and/or trialkyl-aromatic compounds as compared to similar processes that exclusively recycle the second recycle stream to each alkylation reaction. Further, because reaction rates in the at least one primary alkylation reaction tend to be higher than in downstream alkylation reactions, greater rates of by-product formation may be prevalent in the at least one primary alkylation reaction than in the at least one downstream alkylation reaction such that recycling of the first recycle stream to the at least one primary alkylation reaction, in addition to recycling of the second recycle stream, may more effectively minimize dialkyl- and/or trialkyl-aromatic compound formation than can be achieved with modification of recycle dynamics in the at least one downstream alkylation reaction. By recycling the first recycle stream to the at least one primary alkylation reaction, in addition to recycling of the second recycle stream to the at least one primary alkylation reaction, the processes enable the maximum selectivity of monoalkyl aromatic compounds to be achieved without increasing a ratio of aromatic compound to olefin.

Figure 1:
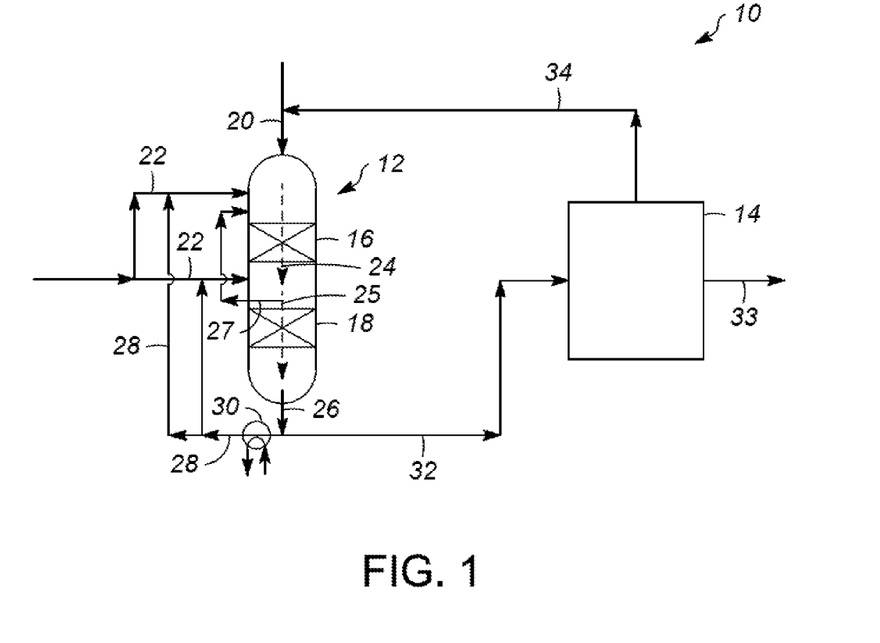
FIG. 1 is a schematic diagram of an alkylation apparatus using an exemplary embodiment of a process for preparing alkylated aromatic compounds.

An exemplary process will now be described with respect to an embodiment of an alkylation apparatus 10 illustrated in FIG. 1. The process includes reacting the aromatic compound and the olefin in at least one primary alkylation reaction in the presence of a first alkylation catalyst to produce a first effluent including an alkylated aromatic compound and an unreacted aromatic compound. As referred to herein, the at least one primary alkylation reaction refers to any alkylation reaction that is upstream of and produces the first effluent. The first effluent refers to reaction effluent that is subsequently split into the first product-rich stream and the first recycle stream, as described in further detail below. For example, as shown in FIG. 1, an aromatic compound 20 and an olefin 22 are introduced into at least one primary alkylation catalyst bed 16 of an alkylation reactor 12, under alkylation conditions, to produce the first effluent 24. In the embodiment shown in FIG. 1, the alkylation reactor 12 includes a single primary alkylation catalyst bed 16. The at least one primary alkylation catalyst bed 16 includes a first alkylation catalyst. The aromatic compound and the olefin may be reacted in at least two primary alkylation reactions, such as from 2 to about 10 primary alkylation reactions, to produce the first effluent. Under such circumstances, an additional olefin may be added to each primary alkylation reaction after a first primary alkylation reaction because the alkylation reactions are generally conducted with a stoichiometric excess of aromatic compound. The olefin and the additional olefin, as referred to herein, are the same but are only distinguishable as being introduced into different alkylation reactions.

In an embodiment, as shown in FIG. 1, the alkylation reactor 12 is a multi-bed alkylation reactor 12 and includes the at least one primary alkylation catalyst bed 16 and at least one downstream alkylation catalyst bed 18. The at least one downstream alkylation catalyst bed 18 refers to any alkylation catalyst bed that is disposed downstream of the at least one primary alkylation catalyst bed 16 and also downstream of the first effluent 24 after splitting the first effluent 24 into the first product-rich stream 25 and the first recycle stream 27, as described in further detail below. In the embodiment shown in FIG. 1, the multi-bed alkylation reactor 12 includes one downstream alkylation catalyst bed 18. Although not shown, it is to be appreciated that in other embodiments, the alkylation apparatus may include multiple alkylation reactors having a single alkylation catalyst bed, with the alkylation reactors arranged in series.

As set forth above, the processes described herein are generally applicable to reaction of aromatic compounds and olefins in the presence of an alkylation catalyst to form an alkylated aromatic compound. Benzene is the aromatic compound of principle interest; however, it is to be appreciated that other aromatic compounds may also be used, such as alkyl-substituted benzenes, polyaromatic compounds such as naphthalene, and the like. Suitable olefins include those having from about 2 to about 20 carbon atoms, with those having from about 2 to about 4 carbon atoms being of principle interest. For example, benzene and ethylene may be reacted to form ethylbenzene as the desired monoalkyl aromatic compound. As another example, benzene and propylene may be reacted to form cumene as the desired monoalkyl aromatic compound.

Suitable alkylation catalysts that may be included in the alkylation catalyst beds 16, 18 are well known in the art, and a wide variety of alkylation catalysts can be used to catalyze the reaction of the aromatic compounds and the olefins. Examples of suitable alkylation catalysts include those characterized as aluminosilicate molecular sieves known as zeolites. Suitable zeolitic molecular sieves are crystalline aluminosilicates which, in the calcined form, may be represented by the general formula:

where Me is a cation, n is the valence of the cation, x has a value of from about 5 to 100, and y has a value of from about 2 to 10. Such zeolites are well-known in the art. Typical well-known zeolites that may be used include Y zeolite, beta zeolite, X zeolite, mordenite, faujasite, zeolite omega, UZM-8, ZSM-5, PSH-3, MCM-22, MCM-36, MCM-49, and MCM-56. The zeolite catalyst will usually be used in combination with a refractory inorganic oxide binder. Examples of inorganic oxide binders include silica and alumina such as, but not limited to, gamma-alumina, eta-alumina, and mixtures thereof.

The aromatic compound reacted in the at least one primary alkylation reaction generally includes fresh aromatic compounds, and may also include aromatic compounds that are provided in a recycle stream that is recycled to the at least one primary alkylation reaction as described in further detail below. "Fresh" aromatic compounds refer to aromatic compounds that are provided from source streams that have not yet passed through the alkylation reaction or that have been separated from reactor effluent from the alkylation reaction. The at least one primary alkylation reaction can be conducted over a broad range of operating conditions, depending upon the particular aromatic compounds and olefins reacted. As one specific example, when producing cumene, the aromatic compound is benzene and the olefin is propylene. The at least one primary alkylation reaction may be conducted to obtain an essentially complete conversion of the propylene to cumene, diisopropylbenzene, or heavier polyisopropylbenzenes, with cumene present in greater amounts than other reaction products. Propylene conversion is generally more than 99% and preferably more than 99.9%. To attain such high propylene conversion, a stoichiometric excess of benzene over propylene is generally present during the at least one primary alkylation reaction. For example, the molar ratio of benzene per propylene is generally from about 20:1 to 1:1, such as from about 5:1 to 1:1, in each alkylation reaction. Temperatures usually range from about 80 to about 327° C., such as from about 110 to about 204° C., in each alkylation reaction. Pressures can also vary within a wide range of from about 1 to about 130 atmospheres (atm). Because the alkylation reactions are generally conducted under liquid phase conditions, the pressure should be sufficient to maintain the benzene at least partially in a liquid phase and may fall in a range of from 15 to 50 atm. The benzene liquid hourly space velocity (LHSV) is generally from about 0.1 to about 50 hr$^{-1}$, such as from about 0.5 to about 10 hr$^{-1}$. The propylene concentration in the at least one primary alkylation reaction is generally less than about 10 mol %, such as less than about 3 mol %.

The process continues with splitting the first effluent into the first product-rich stream and the first recycle stream, as alluded to above. The first product-rich stream and the first recycle stream have the same chemical make-up as the first effluent and are only distinguishable by where the respective streams are sent after splitting. The first recycle stream is recycled to the at least one primary alkylation reaction, and may be recycled only to the at least one primary alkylation reaction. For example, as shown in FIG. 1, where the alkylation reactor 12 only includes a single primary alkylation catalyst bed 16, the first recycle stream 27 is recycled to the single primary alkylation catalyst bed 16. However, when greater than one primary alkylation reaction is employed, the first recycle stream can be recycled to one or more of the primary alkylation reactions.

The process continues with the reaction of unreacted aromatic compound from the first product-rich stream and an additional olefin in at least one downstream alkylation reaction in the presence of a second alkylation catalyst, which can be the same as or different from the first alkylation catalyst, to produce a second effluent that includes the alkylated aromatic compound. As alluded to above, the at least one downstream alkylation reaction refers to any alkylation reaction that is downstream of the at least one primary alkylation reaction and also downstream of the first effluent after splitting the first effluent into the first product-rich stream and the first recycle stream. For example, as shown in FIG. 1, the first product-rich stream 25 and the additional olefin 22 are introduced into the at least one downstream alkylation catalyst bed 18, which includes a second alkylation catalyst, under alkylation conditions to produce a second effluent 26 that includes the alkylated aromatic compound. "Additional" olefin that is reacted in the at least one downstream alkylation reaction refers to olefin that is separately introduced into the at least one downstream alkylation reaction and that is not present during the at least one primary alkylation reaction, but is otherwise the same as the olefin reacted in the at least one primary alkylation reaction. In the embodiment of FIG. 1, the alkylation apparatus 10 includes the multi-bed alkylation reactor 12 having one primary alkylation catalyst bed 16 and one downstream alkylation catalyst bed 18. In this embodiment, the first effluent 24 is formed, separated into the first recycle stream 27 and the first product-rich stream 25, and the first product-rich stream 25 is introduced along with the additional olefin 22 into the downstream alkylation catalyst bed 18 in the multi-bed alkylation reactor 12. In another embodiment, the unreacted aromatic compound from the first product-rich stream and the additional olefin may be reacted in at least two downstream alkylation reactions, such as from 2 to about 10 additional downstream reactions, to produce the second effluent. When producing cumene, additional propylene can be introduced into each downstream alkylation reaction to make up for propylene consumed in the immediately prior alkylation reaction. The aromatic component and olefin are reacted with a temperature rise between alkylation reactions that may be less than or equal to about 50° C., such as less than or equal to about 15° C., which can be controlled through recycling the first recycle stream and a second recycle stream (as described in further detail below) into the various alkylation reactions.

Like the first effluent, the second effluent is also split. In particular, the process continues with splitting the second effluent into a second product-rich stream and a second recycle stream. The second product-rich stream and the second recycle stream have the same chemical make-up as the second effluent and are only distinguishable by where the respective streams are sent after splitting. The second recycle stream is recycled to the at least one primary alkylation reaction and, optionally, the at least one downstream alkylation reaction. In an embodiment, the second recycle stream is recycled to both the at least one primary alkylation reaction and the at least one downstream alkylation reaction. For example, as shown in FIG. 1, the second effluent 26 is split into the second recycle stream 28 and the second product-rich stream 32, and the second recycle stream 28 is recycled to the at least one primary alkylation catalyst bed 16 and the at least one downstream alkylation catalyst bed 18. The recycle stream can be recycled to each primary alkylation reaction or, alternatively, may only be recycled to one primary alkylation reaction. Because the second recycle stream may be employed to control temperature in the at least one primary alkylation reaction and/or at least one downstream alkylation reaction, the second recycle stream may be cooled prior to recycling to the at least one primary alkylation reaction and, optionally, the at least one downstream alkylation reaction, such as through use of a heat exchanger 30 or other cooling device as shown in FIG. 1.

As set forth above, both the first recycle stream and the second recycle stream are recycled to the at least one primary alkylation reaction. In this regard, the first recycle stream may substitute a portion of the second recycle stream recycled to the at least one primary alkylation reaction, as compared to amounts of the second recycle stream that would otherwise be employed in the at least one primary alkylation reaction. Alternatively, the first recycle stream may supplement the second recycle stream recycled to the at least one primary alkylation reaction, with no attendant decrease in an amount of the second recycle stream being recycled to the at least one primary alkylation reaction. In any event, higher amounts of the first recycle stream recycled to the at least one primary alkylation reaction, as compared to amounts of the second recycle stream recycled to the at least one primary alkylation reaction, result in higher selectivity of monoalkyl aromatic compound formation. In an embodiment, the first recycle stream is recycled to the at least one primary alkylation reaction in an amount of at least 10% by weight, such as from about 20 to about 80% by weight, or from about 30 to about 70% by weight, based upon a total combined amount of the first recycle stream and the second recycle stream recycled to the at least one primary alkylation reaction. Such values apply individually to each primary alkylation reaction to which the first recycle stream and the second recycle stream are recycled. Higher amounts of the first recycle stream recycled to the at least one primary alkylation reaction, as compared to amounts of the second recycle stream recycled to the at least one primary alkylation reaction, are more effective for increasing selectivity of monoalkyl aromatic compound formation when the first recycle stream and the second recycle stream are recycled to the at least one primary alkylation reaction at higher mass ratios of total recycle stream to a total mass flow in the at least one primary alkylation reaction. For purposes of this disclosure, "total mass flow" refers to a total amount of all compounds that are introduced into the respective alkylation reactions including the aromatic compound, olefin (or additional olefin), and any compounds that may be present therewith when introduced into the alkylation reactions (including alkylated aromatic compounds, side-product compounds such as n-propylbenzene, non-selective heavy aromatic side products such as diphenylpropane, and the like). In an embodiment, the first recycle stream and the second recycle stream are recycled to the at least one primary alkylation reaction at a ratio of total recycle stream to a total mass flow in the at least one primary alkylation reaction of at least 0.5:1, such as from about 1:1 to about 6:1.

In an embodiment, the second product-rich stream is separated to recover the alkylated aromatic compound therefrom, and also to recover the unreacted aromatic compound therefrom. For example, as shown in FIG. 1, the second product-rich stream 32 is separated in a separating system 14 to produce the alkylated aromatic compound 33 and a return stream 34. Separation techniques are well known in the art and may include subjecting the second product-rich stream to fractionation to separate compounds of different volatilities and, optionally, transalkylation to recover by-products of the alkylation reactions, including multiple alkylated by-products. For example, the separating system 14 of FIG. 1 may include a transalkylation reactor (not shown) and one or more fractionation columns (not shown) for separating alkylated aromatic compounds of different volatilities. The unreacted aromatic compound that is recovered by the separating system 14 may be returned in the return stream 34 to the alkylation reactor 12.

Figure 2:
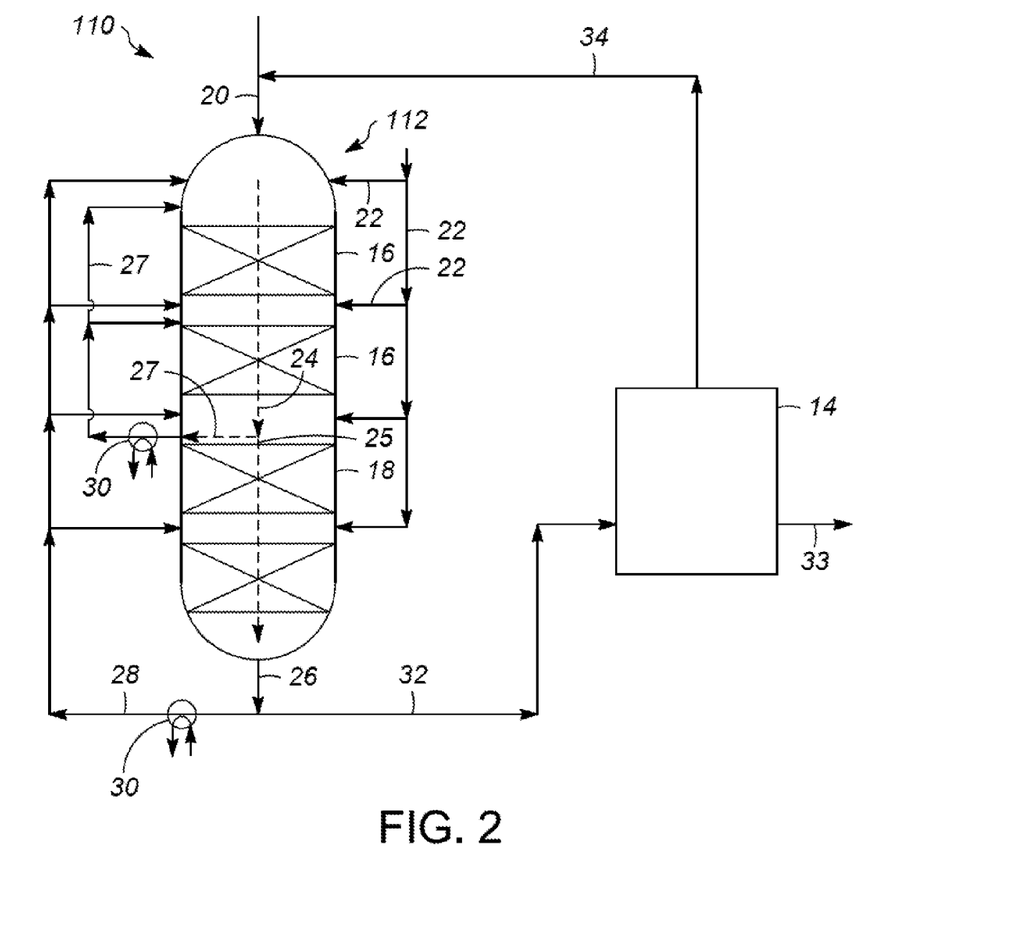
FIG. 2 is a schematic diagram of an alkylation apparatus using another exemplary embodiment of a process for preparing alkylated aromatic compounds.

Another exemplary process will now be described with reference to another alkylation apparatus 110 as shown in FIG. 2. Referring to FIG. 2, the alkylation apparatus 110 includes a multi-bed alkylation reactor 112 including at least one primary alkylation catalyst bed 16 and at least one downstream alkylation catalyst bed 18, similar to the alkylation apparatus 10 of FIG. 1. However, unlike the alkylation apparatus 10 of FIG. 1, the multi-bed alkylation reactor 112 of FIG. 2 includes two primary alkylation catalyst beds 16 and two downstream alkylation catalyst beds 18. In this embodiment, the steps of introducing the aromatic compound 20 and the olefin 22 into the at least one primary alkylation catalyst bed 16 and introducing the first product-rich stream 25 and the additional olefin 22 into the at least one downstream alkylation catalyst bed 18 are conducted in the multi-bed alkylation reactor 112. Because the multi-bed alkylation reactor 112 includes the two primary alkylation catalyst beds 16, introducing the aromatic compound 20 and the olefin 22 into the at least one primary alkylation catalyst bed 16 is further defined as introducing the aromatic compound 20 and the olefin 22 into a first alkylation catalyst bed 16 of the at least two primary alkylation catalyst beds 16, with the effluent from the first alkylation catalyst bed 16 including the alkylated aromatic compound and the unreacted aromatic compound. The additional olefin 22 is introduced into a second primary alkylation catalyst bed 16, along with the effluent from the first alkylation catalyst bed 16, to produce the first effluent 24. The first effluent 24 is then separated into the first recycle stream 27 and the first product-rich stream 25 as described above in the context of the process conducted in the alkylation apparatus 10 of FIG. 1. The first product-rich stream 25 and the additional olefin 22 are introduced into a first downstream alkylation catalyst bed 18, with the effluent therefrom introduced into a second downstream alkylation catalyst bed 18 along with the additional olefin 22 to produce the second effluent 26. The second effluent 26 is separated into the second recycle stream 28 and the second product-rich stream 32, as described above.

Figure 3:
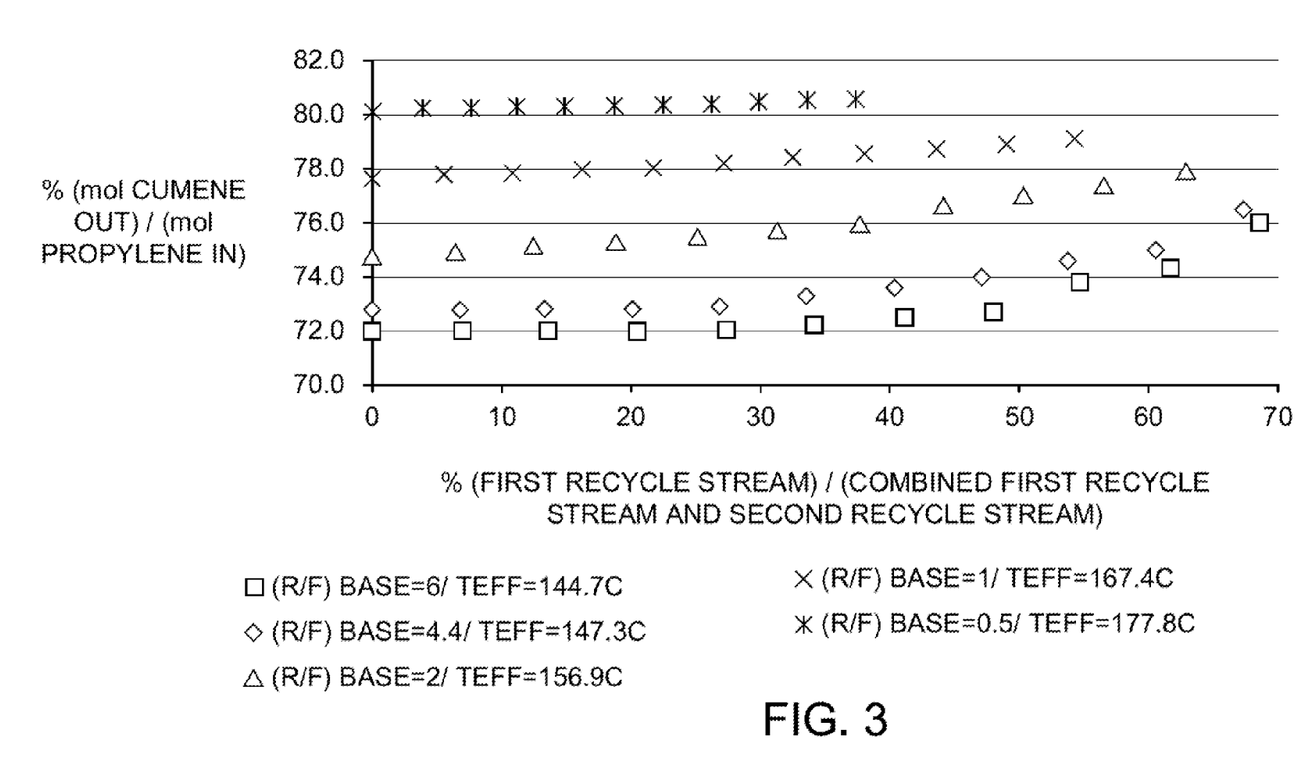
FIG. 3 is a graph illustrating computer-simulated selectivity for production of cumene as a function of combined flow rate of the first recycle stream and the second recycle stream to direct feed flow rate (R/F) and further as a function of first recycle stream as a percentage of the combined amount of first recycle stream and second recycle stream when the alkylation apparatus of FIG. 2 is employed in a process for preparing cumene.

Referring to FIG. 3, computer-simulated results for cumene selectivity are shown when the multi-bed alkylation reactor 112 of FIG. 2 is employed under different process variables. Values along the horizontal axis represent an amount of first recycle stream 27 as a percentage of the combined amount of first recycle stream 27 and second recycle stream 28 recycled to each of the primary alkylation catalyst beds 16. Values along the vertical axis represent selectivity of cumene production, in mol %, based upon the total mols of propylene that are introduced into the multi-bed alkylation reactor 112. The temperature of the recycle streams and olefin 22 fed into each alkylation catalyst bed is maintained at a constant 135° C., with the benzene and propylene reacted at a constant ratio of 2.0 (mol benzene/mol propylene) in each alkylation catalyst bed and with a constant total recycle stream flow rate but with individual recycle stream flow rate to each alkylation catalyst bed adjusted to maintain the same effluent temperature from each alkylation catalyst bed 16, 18. Different data sets were generated based upon different ratios of combined flow rate of the first recycle stream 27 and the second recycle stream 28 to direct feed flow rate (i.e., non-recycle feed flow) in each alkylation catalyst bed 16, 18, which results in a different bed-effluent temperature (TEFF) as shown in FIG. 3. Depending upon the particular ratios of combined flow rate of the first recycle stream 27 and the second recycle stream 28 to direct feed flow rate, an increase in selectivity of up to 4 mol % or more can theoretically be achieved.

Figure 4:
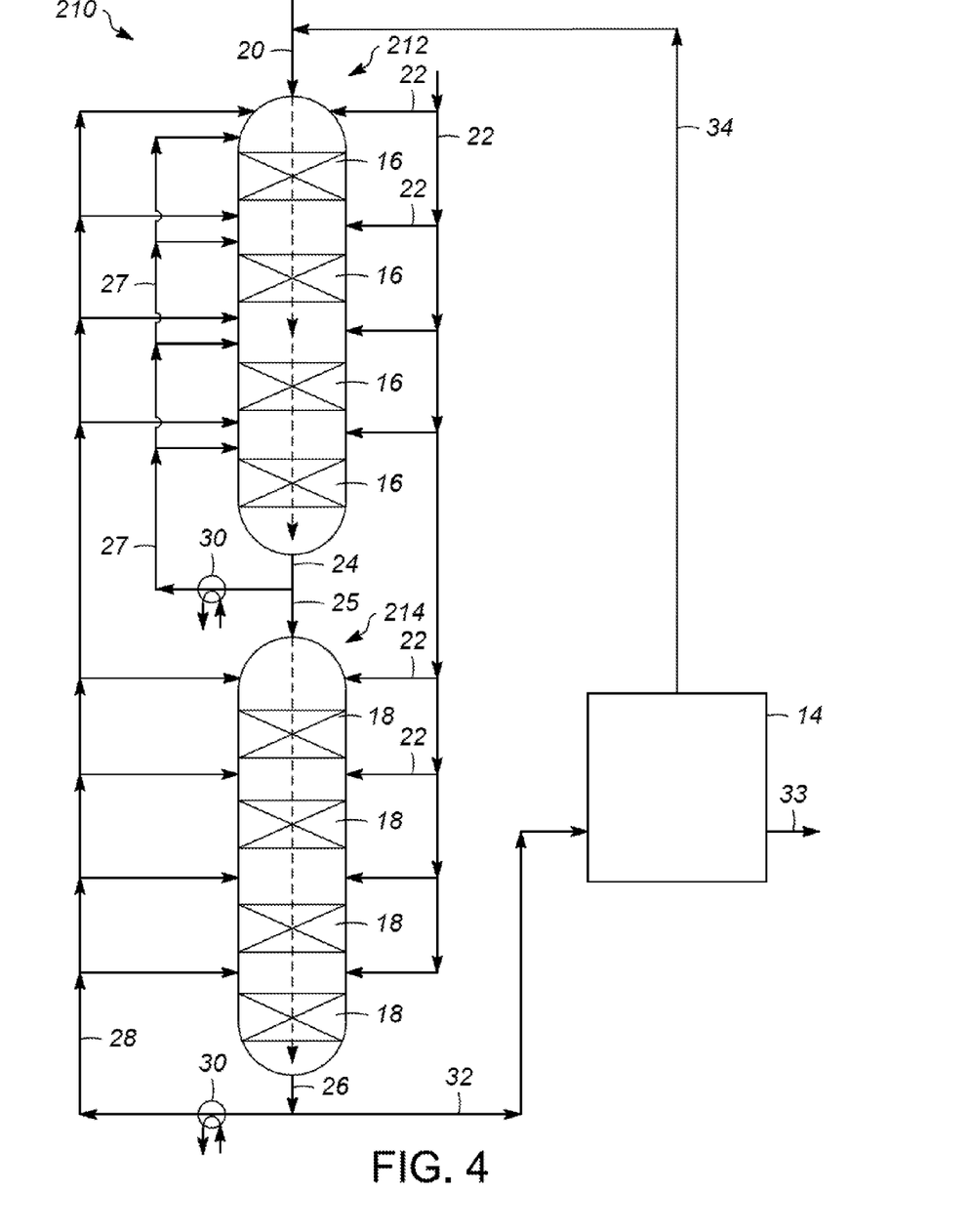
FIG. 4 is a schematic diagram of an alkylation apparatus using another exemplary embodiment of a process for preparing alkylated aromatic compounds.

Another exemplary process will now be described with reference to another alkylation apparatus 210 as shown in FIG. 4. Referring to FIG. 4, the alkylation apparatus 210 includes a first alkylation reactor 212 and a second alkylation reactor 214 in series. In this embodiment, the first alkylation reactor 212 includes the at least one primary alkylation catalyst bed 16 and the second alkylation reactor 214 includes the at least one downstream alkylation catalyst bed 18. In the alkylation apparatus 210 of FIG. 4, the first alkylation reactor 212 is a multi-bed alkylation reactor including four primary alkylation catalyst beds 16 and the second alkylation reactor 214 is also a multi-bed alkylation reactor including four downstream alkylation catalyst beds 18. In this embodiment, the step of introducing the aromatic compound 20 and the olefin 22 into the at least one primary alkylation catalyst bed 16 is conducted in the first alkylation reactor 212 and the step of introducing the first product-rich stream 25 and the additional olefin 22 into the at least one downstream alkylation catalyst bed 18 is conducted in the second alkylation reactor 214. Because the first alkylation reactor 212 of FIG. 4 includes the four primary alkylation catalyst beds 16, introducing the aromatic compound 20 and the olefin 22 into the at least one primary alkylation catalyst bed 16 is further defined as introducing the aromatic compound 20 and the olefin 22 into a first alkylation catalyst bed 16 of the four primary alkylation catalyst beds 16, with the effluent from the first alkylation catalyst bed 16 including the alkylated aromatic compound and the unreacted aromatic compound. The additional olefin 22 is introduced into the subsequent primary alkylation catalyst beds 16, along with the effluent from the immediately preceding primary alkylation catalyst bed 16, to produce the first effluent 24. The first effluent 24 is then separated into the first recycle stream 27 and the first product-rich stream 25 as described above in the context of the process conducted in the alkylation apparatus 10 of FIG. 1. The first product-rich stream 25 and the additional olefin 22 are introduced into a first downstream alkylation catalyst bed 18 of the four downstream alkylation catalyst beds 18 shown in FIG. 4. The additional olefin 22 is introduced into the subsequent downstream alkylation catalyst beds 18, along with the effluent from the immediately preceding downstream alkylation catalyst bed 18, to produce the second effluent 26. The second effluent 26 is separated into the second recycle stream 28 and the second product-rich stream 32, as described above.

Figure 5:
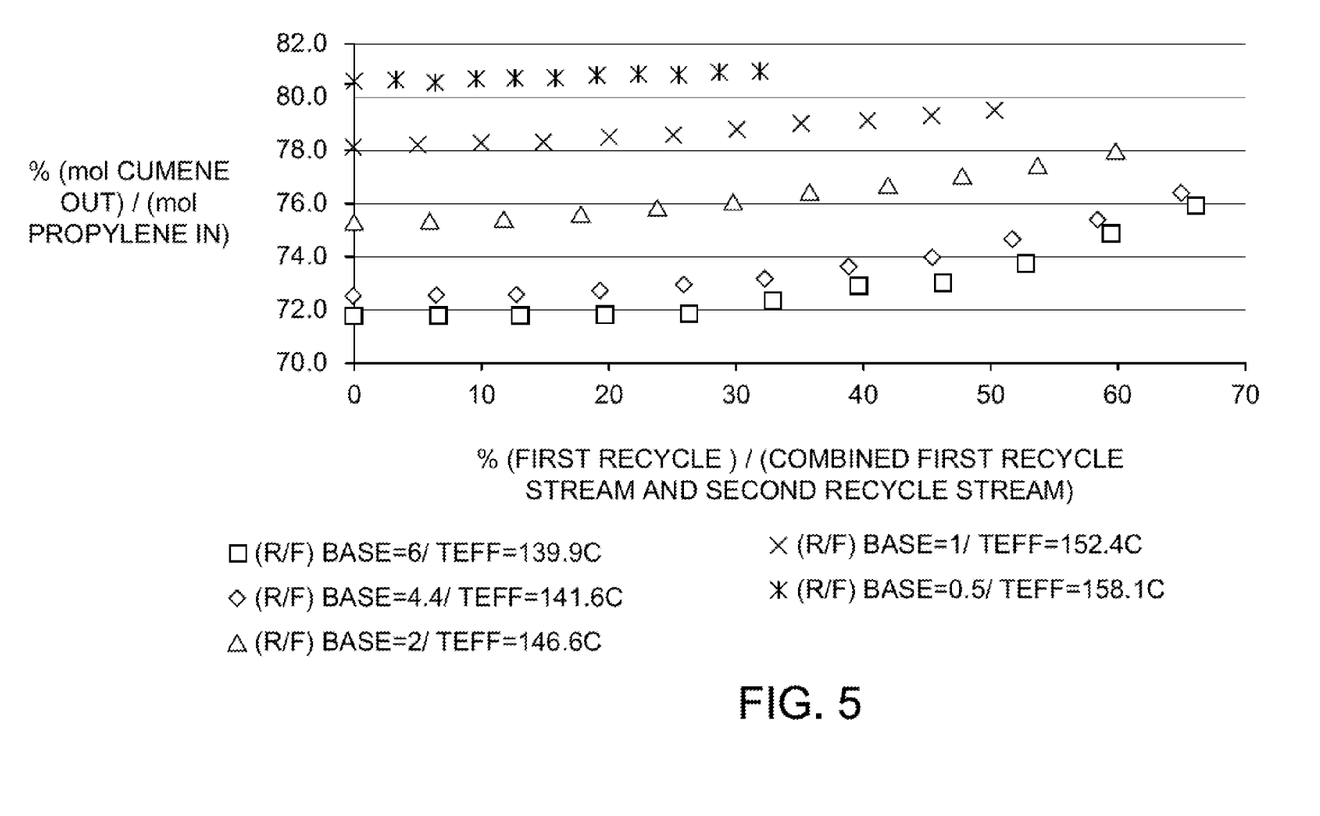
FIG. 5 is a graph illustrating computer-simulated selectivity for production of cumene as a function of combined flow rate of the first recycle stream and the second recycle stream to direct feed flow rate and further as a function of first recycle stream as a percentage of the combined amount of first recycle stream and second recycle stream when the alkylation apparatus of FIG. 4 is employed in a process for preparing cumene.

Referring to FIG. 5, computer-simulated results for cumene selectivity are shown when the first alkylation reactor 212 and the second alkylation reactor 214 of FIG. 4 are employed, and the results were generated as described above in the context of FIG. 3. Depending upon the particular ratios of combined flow rate of the first recycle stream 27 and the second recycle stream 28 to direct feed flow rate, an increase in selectivity of up to 4 mol % or more can also theoretically be achieved, although selectivity toward cumene using the first alkylation reactor 212 and the second alkylation reactor 214 of FIG. 4 is theoretically marginally higher than when using the multi-bed alkylation reactor 112 as shown in FIG. 2.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for preparing alkylated aromatic compounds, the process comprising the steps of:

reacting an aromatic compound and an olefin in at least one primary alkylation reaction in the presence of a first alkylation catalyst to produce a first effluent comprising an alkylated aromatic compound and an unreacted aromatic compound;

splitting the first effluent into a first product-rich stream and a first recycle stream;

recycling the first recycle stream to the at least one primary alkylation reaction;

reacting the unreacted aromatic compound from the first product-rich stream and an additional olefin in at least one downstream alkylation reaction in the presence of a second alkylation catalyst to produce a second effluent comprising the alkylated aromatic compound;

splitting the second effluent into a second product-rich stream and a second recycle stream;

recycling the second recycle stream to the at least one primary alkylation reaction and, optionally, to the at least one downstream alkylation reaction; and wherein the first recycle stream is recycled to the at least one primary alkylation reaction in an amount of at least 20% by weight based upon a total combined amount of the first recycle stream and the second recycle stream recycled to the at least one primary alkylation reaction, and wherein the first recycle stream and the second recycle stream are recycled to the at least one primary alkylation reaction at a ratio of total recycle stream to a total mass flow in the at least one primary alkylation reaction is between 0.5:1 and 6:1, and wherein reacting the aromatic compound and the olefin in the at least one primary alkylation reaction is further defined as reacting benzene with ethylene or propylene to produce the first effluent comprising ethylbenzene or cumene.

2. The process of claim 1, wherein the first recycle stream substitutes a portion of the second recycle stream recycled to the at least one primary alkylation reaction.

3. The process of claim 1, further comprising the step of separating the second product-rich stream to recover the alkylated aromatic compound therefrom.

4. The process of claim 1, wherein reacting the aromatic compound and the olefin in the at least one primary alkylation reaction is further defined as reacting the aromatic compound and the olefin in at least two primary alkylation reactions to produce the first effluent.

5. The process of claim 1, wherein reacting the unreacted aromatic compound from the first product-rich stream and the additional olefin in the at least one downstream alkylation reaction is further defined as reacting the unreacted aromatic compound from the first effluent and the additional olefin in at least two downstream alkylation reactions to produce the second effluent.

6. The process of claim 1, wherein the second recycle stream is recycled to the at least one primary alkylation reaction and to the at least one downstream alkylation reaction.

7. The process of claim 1, wherein the first recycle stream is recycled only to the at least one primary alkylation reaction.

8. The process of claim 1, wherein the aromatic compound and the olefin are reacted with a temperature rise between alkylation reactions of less than or equal to about 50° C.

9. The process of claim 1, wherein reacting the aromatic compound and the olefin in the at least one primary alkylation reaction is further defined as reacting benzene and propylene to produce the first effluent comprising cumene.

10. The process of claim 1, wherein reacting the aromatic compound and the olefin in the at least one primary alkylation reaction is further defined as reacting benzene and ethylene to produce the first effluent comprising ethylbenzene.

11. The process of claim 1, further comprising the step of cooling at least one of the first recycle stream or the second recycle stream prior to recycling to the at least one primary alkylation reaction.

* * * * *